United States Patent [19]

Rasberger et al.

[11] 4,234,723

[45] Nov. 18, 1980

[54] NICKEL STABILIZERS FOR SYNTHETIC POLYMERS

[75] Inventors: Michael Rasberger, Allschwil; Jean Rody, Basel; Paul Moser, Riehen; Helmut Müller, Binningen, all of Switzerland

[73] Assignee: Ciba-Geigy Corporation, Ardsley, N.Y.

[21] Appl. No.: 62,448

[22] Filed: Jul. 30, 1979

Related U.S. Application Data

[62] Division of Ser. No. 827,293, Aug. 24, 1977, Pat. No. 4,186,267, which is a division of Ser. No. 663,332, Mar. 3, 1976, Pat. No. 4,046,788, which is a division of Ser. No. 491,978, Jul. 26, 1974, Pat. No. 3,948,852.

[30] Foreign Application Priority Data

Aug. 7, 1973 [CH] Switzerland .................. 11407/73
Jan. 28, 1974 [CH] Switzerland .................... 1103/74

[51] Int. Cl.$^3$ ............................................. C07F 15/04

[52] U.S. Cl. ............................................................ 544/64
[58] Field of Search ............................................. 544/64

[56] References Cited

U.S. PATENT DOCUMENTS

| | | | |
|---|---|---|---|
| 3,189,630 | 6/1965 | Smutny | 260/439 |
| 3,901,931 | 8/1975 | Rasberger et al. | 544/64 |
| 3,948,852 | 4/1976 | Rasberger et al. | 260/439 R |
| 4,046,788 | 9/1977 | Rasberger et al. | 260/439 R |

*Primary Examiner*—Henry R. Jiles
*Assistant Examiner*—R. W. Ramsuer
*Attorney, Agent, or Firm*—Harry Falber

[57] ABSTRACT

Nickel complexes containing ortho- or para-hydroxybenzoate anions and a non-ionic amine ligand are valuable light-stabilizers for polymers, particularly for polyolefins. The complexes may also contain a second carboxylate anion, different from the benzoate anion, and in this case also the amine-free nickel compounds show a high stabilizing action.

5 Claims, No Drawings

NICKEL STABILIZERS FOR SYNTHETIC POLYMERS

This is a divisional of application Ser. No. 827,293, filed on Aug. 24, 1977, now U.S. Pat. No. 4,186,267, which is a divisional application of Ser. No. 663,332, filed Mar. 3, 1976, now U.S. Pat. No. 4,046,788, which is a divisional application of Ser. No. 491,978, filed July 26, 1974, now U.S. Pat. No. 3,948,852.

The invention relates to new nickel complexes of hydroxybenzoic acids, their preparation, their use as light stabilisers and/or as dyestuff receptors for polymeric substrates and, as an industrial product, the polymers which contain the compounds claimed.

The subject of the invention are compounds of the formula I

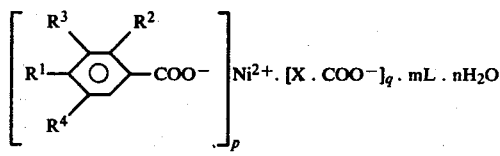

wherein either $R^1$ is hydroxyl and $R^2$ is hydrogen or $R^1$ is hydrogen and $R^2$ is hydroxyl, $R^3$ and $R^4$ are hydrogen or alkyl with 1–5 C atoms, either p is 1 and q is 1 or p is 2 and q is zero, X is optionally hydroxyl-substituted alkyl, cycloalkyl, aryl, alkaryl or aralkyl, m is a value from 1 to 2 and, if q=1, can also be zero, n represents a value from 0 to 2 and L denotes a ligand $R^5$—N($R^6$)—$R^7$, in which $R^5$ represents alkyl, alkoxyalkyl, alkylthioalkyl, aryl, aralkyl or cycloalkyl and $R^6$ represents H, alkyl, aralkyl or cycloalkyl or $R^5$ and $R^6$ together with the N atom form a pyrrolidine, piperidine or morpholine ring which is substituted by alkyl groups or is unsubstituted, and $R^7$ is H, alkyl or aralkyl.

Preferred compounds of the formula I are those wherein $R^1$, $R^2$, $R^3$, $R^4$, m and n have the abovementioned meaning and L denotes a ligand $R^5$—N($R^6$)—$R^7$, in which $R^5$ represents alkyl with 4 to 18 C atoms, aryl with 6 to 18 C atoms, aralkyl with 7 to 19 C atoms or cycloalkyl with 5 to 10 C atoms and $R^6$ represents H, alkyl with 1 to 18 C atoms, aralkyl with 7 to 19 C atoms or cycloalkyl with 5 to 10 C atoms or $R^5$ and $R^6$ together with the N atom form a piperidine or morpholine ring which is substituted by methyl groups or is unsubstituted, and $R^7$ is H, alkyl with 1–8 C atoms or aralkyl with 7–11 C atoms and either p is 1 and q is 1 or p is 2 and q is zero, and X is alkyl or hydroxyalkyl with 1–22 C atoms, cycloalkyl with 4–10 C atoms, phenyl which is optionally substituted by alkyl with 1–4 C atoms and/or hydroxyl, or phenylalkyl with 7–16 C atoms.

Particularly preferred compounds of the formula I are those wherein $R^1$ is hydroxyl, $R^2$ is hydrogen and $R^3$ and $R^4$ are each tertiary butyl, m is the number 1 or zero, n denotes a value from 0 to 2 and L denotes a ligand $R^5$—N($R^6$)—$R^7$, in which $R^5$ represents alkyl with 4 to 18 C atoms, aralkyl with 7 to 19 C atoms or cycloalkyl with 5 to 10 C atoms and $R^6$ represents H, alkyl with 1 to 18 C atoms or cycloalkyl with 5 to 10 C atoms or $R^5$ and $R^6$ together with the N atom form a 2,2,6,6-tetramethylpiperidine ring and $R^7$ is H or alkyl with 1 to 8 C atoms, and either p is 1 and q is 1 or p is 2 and q is zero, and X is alkyl with 1 to 18 C atoms.

For example, the invention relates to compounds of the formula I, wherein either $R^1$ represents a hydroxyl group and $R^2$ represents hydrogen or $R^1$ represents hydrogen and $R^2$ represents a hydroxyl group, $R^3$ and $R^4$ represent hydrogen or alkyl with 1 to 5 C atoms, m represents a value from 1 to 2 and n represents a value from 0 to 2 and L denotes a ligand of the formula $R^5$—N($R^6$)—$R^7$, in which $R^5$ represents alkyl, aryl, aralkyl or cycloalkyl and $R^6$ represents H, alkyl, aralkyl or cycloalkyl or $R^5$ and $R^6$ together with the N atom form a pyrrolidine, piperidine or morpholine ring which is substituted by alkyl groups or is unsubstituted, and $R^7$ is H, alkyl or aralkyl, and p is 2 and q is zero.

Further preferred compounds of the formula I are those wherein $R^1$, $R^2$, $R^3$, $R^4$, m and n have the abovementioned meaning and L denotes a ligand of the formula $$R^5-N(R^6)-R^7$$

in which $R^5$ represents alkyl with 4 to 18 C atoms, aryl with 6 to 18 C atoms, aralkyl with 7 to 19 C atoms or cycloalkyl with 5 to 10 C atoms and $R^6$ represents H, alkyl with 1 to 18 C atoms, aralkyl with 7 to 19 C atoms or cycloalkyl with 5 to 10 C atoms or $R^5$ and $R^6$ together with the N atom form a piperidine or morpholine ring which is substituted by methyl groups or is unsubstituted, and $R^7$ is H, alkyl with 1 to 8 C atoms or aralkyl with 7 to 11 C atoms, and p is 2 and q is zero.

Particularly preferred compounds of the formula I are those wherein $R^1$ denotes hydroxyl, $R^2$ denotes hydrogen, $R^3$ and $R^4$ each denote a tertiary butyl group, m denotes the number 1, n denotes a value from 0 to 2 and L denotes a ligand of the formula $$R^5-N(R^6)-R^7$$

in which $R^5$ represents alkyl with 4 to 18 C atoms, aralkyl with 7 to 19 C atoms or cycloalkyl with 5 to 10 C atoms and $R^6$ represents H, alkyl with 1 to 18 C atoms or cycloalkyl with 5 to 10 C atoms or $R^5$ and $R^6$ together with the N atom form a 2,2,6,6-tetramethylpiperidine ring and $R^7$ is H or alkyl with 1 to 8 C atoms, p is 2 and q is zero.

If $R^1$ is hydroxyl, the compounds of the formula I are complex nickel salts of p-hydroxybenzoic acid or of alkylated p-hydroxybenzoic acids. If $R^2$ is hydroxyl, the compounds are complex nickel salts of salicylic acid or of alkylated salicylic acids.

If $R^3$ and $R^4$ are alkyl groups with 1–5 C atoms, they are, for example, a methyl, ethyl, n-propyl, iso-propyl, n-butyl, tert.butyl or 1,1-dimethylpropyl group.

The complex ligand L is an amine of which the substituents $R^5$, $R^6$ and $R^7$, when they denote alkyl, can be, for example, methyl, ethyl, iso-propyl, sec.butyl, n-hexyl, n-octyl, n-decyl, n-dodecyl or n-octadecyl. When the substituents denote aralkyl they can be, for example, benzyl, 4-methylbenzyl, 4-tert.butylbenzyl or 4-dodecylbenzyl. $R^5$ can also be alkoxyalkyl or alkylthioalkyl, such as β-methoxyethyl, γ-ethoxypropyl, γ-butylthiopropyl or δ-methoxybutyl.

$R^5$ and $R^6$ can also denote cycloalkyl, which can be, for example, cyclopentyl, cyclohexyl, 4-methylcyclohexyl or 4-tert.butylcyclohexyl. $R^5$ can also denote aryl, which can be, for example, phenyl, tolyl, xylyl, tert.butylphenyl or dodecylphenyl.

$R^5$ and $R^6$ together with the N atom of the ligand L can form a pyrrolidine, piperidine or morpholine ring which is substituted by alkyl groups or is unsubstituted. This ring can be, for example, a 2,5-dimethylpyrrolidine, 4-methylpiperidine, 2,2,6,6-tetramethylpiperidine, 2,6-dimethylmorpholine, pyrrolidine, piperidine or morpholine ring.

The ligand L thus represents, according to the definition, a primary, secondary or tertiary amine which is capable of forming a complex with the nickel salt of a hydroxybenzoic acid. Examples of such amines are: n-butylamine, n-dodecylamine, β-ethylhexylamine, benzylamine, 4-octylbenzylamine, dibutylamine, dicyclohexylamine, dioctadecylamine, morpholine, 2,2,6,6-tetramethylpiperidine, n-ethylaniline, tri-n-octylamine, N,N-dimethylaniline, N,N-dimethyl-cyclohexylamine, N-ethylpiperidine, N-methylpyrrolidine, dibenzylpropylamine, N-benzyl-2,5-dimethylpyrrolidine or 2-methoxypropylamine.

The complexes according to the invention, of the formula I, contain 0 or 1 to 2 mols of the amine ligand L per mol of nickel hydroxybenzoate. This molar proportion, expressed by m in the formula I, does not have to be an integer, since the coordination positions of the nickel can in part be occupied by water. The water can be bound coordinatively to the central atom or can be present as water of crystallisation. Its molar proportion n can therefore assume any desired value between 0 and 2. Complexes of low water content are preferred, since these dissolve more readily in non-polar polymers than do more strongly hydrated complexes.

The complexes according to the invention, of the formula I, with p=1 and q=1 contain, as X, if this denotes optionally hydroxy-substituted alkyl, in particular optionally hydroxy-substituted alkyl with 1–22 C atoms, above all alkyl or hydroxyalkyl with 1–18 C atoms, such as, for example, propyl, heptyl, 2-ethylpentyl, undecyl, heptadecyl or 11-hydroxyheptadecyl. If X denotes optionally hydroxy-substituted cycloalkyl, it can be, above all, cycloalkyl with 4–10 C atoms, such as, for example, cyclopentyl, methylcyclopentyl, cyclohexyl or 4-butylcyclohexyl. If X denotes optionally hydroxy-substituted aryl, alkaryl or aralkyl it can be, in particular, a phenyl or phenylalkyl group which is optionally substituted by alkyl with 1–4 C atoms and/or hydroxyl. Examples thereof are the groups phenyl, tolyl, 4-butylphenyl, 2-hydroxyphenyl, 4-hydroxy-3,5-di-tert.butylphenyl, benzyl, phenethyl, 4-hydroxyphenethyl or 4-hydroxy-3,5-di-tert.-butylphenethyl. The presence of a carboxylate anion [X.COO⁻] in the complexes of the formula I can, depending on the choice of X, improve the solubility of the complexes in the particular substrates or can additionally impart to the complexes, which are active as light stabilisers, an anti-oxidative stabiliser action, or can have some other advantage. Where such an additional action is not necessary, the complexes with q=zero will advantageously be used.

The compounds of the formula I, used as individual compounds or as mixtures, are outstanding stabilisers for polymers, especially for polyolefines, to prevent their light-induced degradation, and are good receptors for dyestuffs which can be chelated.

It was already known to stabilise polyolefines with simple nickel benzoates. Surprisingly, however, the new nickel complexes possess greater heat stability than these salts. They can therefore be used at elevated temperature without the polyolefines undergoing the discolouration caused by the previously known nickel benzoates.

Furthermore, the new nickel complexes show a stronger light stabilising action than the previously known nickel benzoates, inspite of having a lower nickel content. They are also superior to the known benzoates as dyestuff receptors. Above all, however, they are superior to the known nickel benzoates in the field of stabilising polyethylene, since the compounds according to the invention, of the formula I, easily dissolve in this substrate and do not tend to exude.

Further, complexes of nickel with thiobisphenols and amines have already been disclosed as stabilisers for polyolefines. Compared to these compounds, the new nickel complexes of the formula I show a substantially better light-stabilising action.

Polymeric substrates which are protected against degradation by the nickel complexes of the the formula I are above all poly-α-olefines, such as polyethylene, crosslinked polyethylene, polypropylene, polyisobutylene, polymethylbutene-1, polymethylpentene-1, polybutene-1, polyisoprene and polybutadiene as well as polystyrene and its copolymers such as, for example, polyacrylonitrile-styrene copolymers or polyacrylonitrile-butadiene-styrene copolymers; copolymers of the olefines, such as ethylene-propylene copolymers and propylene-butene-1 copolymers, as well as terpolymers of ethylene and propylene with a diene such as, for example, hexadiene, dicyclopentadiene or ethylidenenorbornene; mixtures of the abovementioned homopolymers such as, for example, mixtures of polypropylene and polyethylene, polypropylene and polybutene-1 and polypropylene and polyisobutylene. Polypropylene and its mixtures, and the copolymers which contain propylene units, and polyethylene are preferred.

The compounds of the formula I are incorporated into the substrates in a concentration of 0.01 to 5% by weight calculated relative to the material to be stabilised. Preferably, 0.05 to 1.5, and particularly preferentially 0.1 to 0.8, % by weight of the compounds, calculated relative to the material to be stabilised, are incorporated into the latter.

The incorporation can take place after polymerisation, for example by mixing at least one of the compounds of the formula I, and optionally further additives, into the melt in accordance with the methods customary in the art, before or during moulding, or by applying the dissolved or dispersed compounds to the polymer, if necessary with subsequent evaporation of the solvent.

The compounds of the formula I can also be incorporated into the polymer to be stabilised in the form of a master batch which contains the nickel stabiliser in, for example, a concentration of 2.5 to 25% by weight.

In the case of crosslinked polyethylene, the compounds are added before crosslinking. The following should be mentioned as further additives together with which the stabilisers usable according to the invention can be employed:

1. ANTIOXIDANTS 1.1 Simple 2,6-dialkylphenols such as, for example, 2,6-ditert.butyl-4-methylphenol, 2-tert.butyl-4,6-dimethylphenol, 2,6-ditert.butyl-4-methoxymethylphenol and 2,6-dioctadecyl-4-methylphenol.

1.2 Derivatives of alkylated hydroquinones such as, for example, 2,5-ditert.butyl-hydroquinone, 2,5-ditert.amyl-hydroquinone, 2,6-ditert.butyl-hydroquinone, 2,5-ditert.butyl-4-hydroxy-anisole, 3,5-ditert.butyl-4-hydroxy-anisole, tris-(3,5-ditert.butyl-4-hydroxyphenyl)-phosphite, 3,5-ditert.butyl-4-hydroxyphenylstearate and bis-(3,5-ditert.butyl-4-hydroxyphenyl)-adipate.

1.3 Hydroxylated thiodiphenyl ethers such as, for example, 2,2'-thio-bis-(6-tert.butyl-4-methylphenol), 2,2'-thio-bis-(4-octylphenol), 4,4'-thio-bis-(6-tert.butyl-3-methylphenol), 4,4'-thio-bis-(3,6-di-sec.amylphenol), 4,4'-thio-bis-(6-tert.butyl-2-methylphenol) and 4,4'-bis-(2,6-dimethyl-4-hydroxyphenol)-disulphide.

1.4 Alkylidene-bisphenols such as, for example, 2,2'-methylene-bis-(6-tert.butyl-4-methylphenol), 2,2'-methylene-bis-(6-tert.butyl-4-ethylphenol), 4,4'-methylene-bis-(6-tert.butyl-2-methylphenol), 4,4'-methylene-bis-(2,6-ditert.butylphenol), 2,6-di-(3-tert.butyl-5-methyl-2-hydroxybenzyl)-4-methylphenol, 2,2'-methylene-bis-[4-methyl-6-(α-methylcyclohexyl)-phenol], 1,1-bis-(3,5-dimethyl-2-hydroxyphenyl)-butane, 1,1-bis-(5-tert.butyl-4-hydroxy-2-methylphenyl)-butane, 2,2-bis-(5-tert.butyl-4-hydroxy-2-methylphenyl)-butane, 2,2-bis-(3,5-di-tert.butyl-4-hydroxyphenyl)-propane, 1,1,3-tris-(5-tert.butyl-4-hydroxy-2-methylphenyl)-butane, 2,2-bis-(5-tert.butyl-4-hydroxy-2-methylphenyl)-4-n-dodecylmercapto-butane, 1,1,5,5-tetra-(5-tert.butyl-4-hydroxy-2-methylphenyl)-pentane and ethylene-glycol-bis-[3,3-bis-(3'-tert.butyl-4'-hydroxyphenyl)-butyrate].

1.5 O-, N- and S-benzyl compounds such as, for example, 3,5,3',5'-tetra-tert.butyl-4,4'-dihydroxydibenzyl ether, 4-hydroxy-3,5-dimethylbenzyl-mercaptoacetic acid octadecyl ester, tri-(3,5-di-tert.butyl-4-hydroxybenzyl)-amine and bis-(4-tert.butyl-3-hydroxy-2,6-dimethylbenzyl)-dithiol terephthalate.

1.6 Hydroxybenzylated malonic esters such as, for example, 2,2-bis-(3,5-di-tert.butyl-2-hydroxybenzyl)-malonic acid dioctadecyl ester, 2-(3-tert.butyl-4-hydroxy-5-methylbenzyl)-malonic acid dioctadecyl ester, 2,2-bis-(3,5-di-tert.butyl-4-hydroxybenzyl)-malonic acid didodecylmercaptoethyl-ester and 2,2-bis-(3,5-di-tert.butyl-4-hydroxybenzyl)-malonic acid di-[4-(1,1,3,3-tetramethylbutyl)-phenyl]-ester.

1.7 Hydroxybenzyl-aromatics such as, for example, 1,3,5-tri-(3,5-di-tert.butyl-4-hydroxybenzyl)-2,4,6-trimethylbenzene, 1,4-di-(3,5-di-tert.butyl-4-hydroxybenzyl)-2,3,5,6-tetramethylbenzene and 2,4,6-tri-(3,5-di-tert.butyl-4-hydroxybenzyl)-phenol.

1.8 s-Triazine compounds such as, for example, 2,4-bis-octylmercapto-6-(3,5-di-tert.butyl-4-hydroxyanilino)-s-triazine, 2-octylmercapto-4,6-bis-(3,5-di-tert.butyl-4-hydroxy-anilino)-s-triazine, 2-octylmercapto-4,6-bis-(3,5-di-tert.butyl-4-hydroxy-phenoxy)-s-triazine, 2,4,6-tris-(3,5-di-tert.butyl-4-hydroxyphenoxy)-s-triazine, 2,4,6-tris-(3,5-di-tert.butyl-4-hydroxyphenylethyl)-s-triazine and 1,3,5-tris-(3,5-di-tert.butyl-4-hydroxybenzyl)-isocyanurate.

1.9 Amides of β-(3,5-di-tert.butyl-4-hydroxyphenyl)-propionic acid such as, for example, 1,3,5-tris-(3,5-di-tert.butyl-4-hydroxyphenyl-propionyl)-hexahydro-s-triazine and N,N'-di-(3,5-di-tert.butyl-4-hydroxyphenyl-propionyl)-hexamethylenediamine.

1.10 Esters of β-(3,5-di-tert.butyl-4-hydroxyphenyl)-propionic acid with monohydric or polyhydric alcohols, such as, for example, methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thiaundecanol, 3-thiapentadecanol, trimethylhexanediol, trimethylolethane, trimethylolpropane, trishydroxyethylisocyanurate and 4-hydroxymethyl-1-phospha-2,6,7-trioxabicyclo[2,2,2]octane.

1.11 Esters of β-(5-tert.butyl-4-hydroxy-3-methylphenyl)-propionic acid with monohydric or polyhydric alcohols such as, for example, methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thiaundecanol, 3-thiapentadecanol, trimethyl hexanediol, trimethylolethane, trimethylolpropane, trishydroxyethylisocyanurate and 4-hydroxymethyl-1-phospha-2,6,7-trioxabicyclo[2,2,2]octane.

1.12 Esters of 3,5-ditert.butyl-4-hydroxyphenylacetic acid with monohydric or polyhydric alcohols such as, for example, methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thiaundecanol, 3-thiapentadecanol, trimethylhexanediol, trimethylolethane, trimethylolpropane, trishydroxyethylisocyanurate and 4-hydroxymethyl-1-phospha-2,6,7-trioxabicyclo[2,2,2]octane.

1.13 Acylaminophenols such as, for example, N-(3,5-ditert.butyl-4-hydroxyphenyl)-stearic acid amide and N,N'-di-(3,5-ditert.butyl-4-hydroxyphenyl)-thio-bis-acetamide.

1.14 Benzylphosphonates such as, for example, 3,5-ditert.butyl-4-hydroxybenzyl-phosphonic acid dimethyl ester, 3,5-di-tert.butyl-4-hydroxybenzyl-phosphonic acid diethyl ester, 3,5-ditert.butyl-4-hydroxybenzyl-phosphonic acid dioctadecyl ester and 5-tert.butyl-4-hydroxy-3-methylbenzyl-phosphonic acid dioctadecyl ester.

1.15 Aminoaryl derivatives, such as, for example, phenyl-1-naphthylamine, phenyl-2-naphthylamine, N,N'-diphenyl-p-phenylenediamine, N,N'-di-2-naphthyl-p-phenylenediamine, N,N'-di-sec.butyl-p-phenylenediamine, 6-ethoxy-2,2,4-trimethyl-1,2-dihydroquinoline, 6-dodecyl-2,2,4-trimethyl-1,2-dihydroquinoline, monooctyliminodibenzyl and dioctyliminodibenzyl and polymerised 2,2,4-trimethyl-1,2-dihydroquinoline.

2. UV ABSORBERS AND LIGHT STABILISERS 2.1. 2-(2'-Hydroxyphenyl)-benztriazoles, such as, for example, the 5'-methyl-, 3',5'-di-tert.butyl-, 5'-tert.butyl-, 5'-(1,1,3,3-tetramethylbutyl)-, 5-chloro-3',5'-di-tert.butyl-, 5-chloro-3'-tert.butyl-5'-methyl-, 3'-sec.-butyl-5'-tert.butyl-, 3'-α-methylbenzyl-5'-methyl-, 3'-α-methylbenzyl-5'-methyl-5-chloro-, 4'-hydroxy-, 4'-methoxy-, 4'-octoxy-, 3',5'-di-tert.amyl-, 3'-methyl-5'-carbomethoxyethyl- and 5-chloro-3',5'-di-tert.-amyl-derivative.

2.2. 2,4-Bis-(2'-hydroxyphenyl)-6-alkyl-s-triazines, such as, for example, the 6-ethyl-, 6-heptadecyl or 6-undecyl-derivative.

2.3. 2-Hydroxy-benzophenones, such as, for example, the 4-hydroxy-, 4-methoxy-, 4-octoxy-, 4-decyloxy-, 4-dodecyloxy-, 4-benzyloxy-, 4,2',4'-trihydroxy- or 2'-hydroxy-4,4'-dimethoxy-derivative.

2.4. 1,3-Bis-(2'-hydroxy-benzoyl)-benzenes, such as, for example, 1,3-bis-(2'-hydroxy-4'-hexyloxy-benzoyl)-benzene, 1,3-bis-(2'-hydroxy-4'-octyloxy-benzoyl)-benzene and 1,3-bis-(2'-hydroxy-4'-dodecyloxy-benzoyl)-benzene.

2.5. Esters of optionally substituted benzoic acids such as, for example, phenyl salicylate, octylphenyl salicylate, dibenzoylresorcinol, bis-(4-tert.butylbenzoyl)-resorcinol, benzoylresorcinol and 3,5-di-tert.-butyl-4-hydroxybenzoic acid 2,4-di-tert.butyl-phenyl ester or octadecyl ester or 2-methyl-4,6-di-tert.butyl-phenyl ester.

2.6. Acrylates, such as, for example, α-cyano-β,β-diphenylacrylic acid ethyl ester or isooctyl ester, α-carbomethoxycinnamic acid methyl ester, α-cyano-β-methyl-p-methoxy-cinnamic acid methyl ester or butyl ester and N-(β-carbomethoxy-vinyl)-2-methyl-indoline.

2.7. Sterically hindered amines, such as, for example, 4-benzoyloxy-2,2,6,6-tetramethylpiperidine, 4-stearoyloxy-2,2,6,6-tetramethylpiperdine, bis-(2,2,6,6-tetramethylpiperidyl)sebacate and 3-n-octyl-7,7,9,9-tetramethyl-1,3,8-triazaspiro[4,5]decane-2,4-dione.

2.8. Oxalic acid diamides, such as, for example, 4,4'-di-octyloxy-oxanilide, 2,2'-di-octyloxy-5,5'-di-tert.butyl-oxanilide, 2,2'-di-dodecyloxy-5,5'-di-tert.butyl-oxanilide, 2-ethoxy-2'-ethyl-oxanilide, N,N'-bis-(3-dimethylaminopropyl)oxalamide, 2-ethoxy-5-tert.butyl-2'-ethyl-oxanilide and its mixture with 2-ethoxy-2'-ethyl-5,4'-di-tert.butyl-oxanilide and mixtures of ortho- and para-methoxy- as well as of o- and p-ethoxy-disubstituted oxanilides.

3. Phosphites, such as, for example, triphenyl phosphite, diphenylalkyl phosphites, phenyldialkyl phosphites, tri-(nonylphenyl) phosphite, trilauryl phosphite, tri-octadecyl phosphite, 3,9-di-isodecyloxy-2,4,8,10-tetraoxa-3,9-diphosphaspiro[5,5]undecane and tri-(4-hydroxy-3,5-di-tert.butylphenyl)-phosphite.

4. Compounds which destroy peroxide, such as, for example, esters of β-thiodipropionic acid, for example the lauryl, stearyl, myristyl or tridecyl esters, salts of 2-mercaptobenzimidazole, for example the Zn salt, and diphenylthiourea.

5. Basic co-stabilisers, such as, for example, melamine, benzoguanamine, polyvinylpyrrolidone, dicyandiamide, triallyl cyanurate, urea derivatives, hydrazine derivatives, amines, polyamides, polyurethanes, and alkali metal salts and alkaline earth metal salts of higher fatty acids, for example Ca stearate, Zn stearate, Mg stearate, Na ricinoleate or K palmitate.

6. Nucleating agents, such as, for example 4-tert.butyl-benzoic acid, adipic acid and diphenylacetic acid.

7. Other additives, such as, for example, plasticisers, lubricants, emulsifiers, fillers, carbon black, asbestos, kaolin, talc, glass fibres, pigments, flameproofing agents and antistatic agents.

The compounds of the formula I can be prepared according to known processes. The most important method is the reaction of m mols of an amine of the formula L with a nickel compound of the formula II

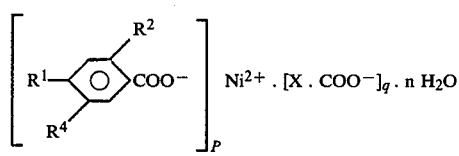

wherein the individual symbols have the same meaning as has been defined for the formula I. In the case of p=2 and q=zero, the compounds (II) are known compounds which can be prepared, for example, by the process of U.S. Pat. No. 3,189,630.

In the case of p=1 and q=1, the compounds (II) can be prepared by reaction of 1 mol of each of the two carboxylic acid components, in the form of the free acids or of their salts, with 1 mol of a nickel salt, such as, for example, $NiCl_2.6\ H_2O$ or $NiCO_3$.

The reaction of the amine with (II) is suitably carried out by adding the amine L to a solution of the nickel compound of the formula II and warming the reaction solution. Suitable solvents for this purpose are alcohols such as methanol, ethanol or ethylene glycol monoalkyl ethers; further examples of suitable solvents are dioxane, tetrahydrofurane, benzene, toluene or acetonitrile.

The greenish-coloured crystalline complexes can be isolated by crystallisation in the cold, or by evaporation of the reaction solution. The water content can be regulated by drying the complexes which have been isolated. However, it can also be regulated by distilling off water as an azeotrope with a part of the solvent during the reaction; for this purpose, toluene or xylene, above all, are suitable solvents. In this way the desired molar proportion n in the complex I is brought about. The molar proportion m results from the molar ratio in which the amine L is added during the reaction.

The compounds I can furthermore also be prepared in one step by reacting the corresponding carboxylic acid components or their salts with a nickel salt, optionally in the presence of water, and optionally adding a corresponding amine.

The reaction takes place in accordance with the equation:

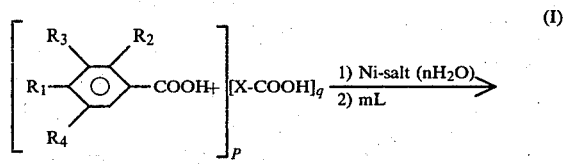

Suitable nickel salts are, for example, nickel chloride or nickel carbonate. The reaction is advantageously carried out in a solvent, such as in an alcohol, for example methanol, ethanol or 2-methoxyethanol, in an ether, such as dioxane or tetrahydrofurane, in an aromatic hydrocarbon, such as benzene or toluene, or in a strongly polar solvent, such as dimethylformamide or acetonitrile. The reaction is preferably carried out at elevated temperature, advantageously at 30°–100° and especially 50°–80°. The water which may be required can advantageously also be employed in the form of water of crystallisation of one of the salts employed, for example of the nickel salt.

The preparation and use of the compounds of the formula I is described in more detail in the examples which follow. In these, percentages (%) denote percentages by weight and parts denote parts by weight.

EXAMPLE 1

28.7 g of nickel 3,5-di-tert.butyl-4-hydroxybenzoate, which contains 4.1% of water, are dissolved in 250 ml of absolute ethanol and a solution of 13.5 g of octadecylamine in 100 ml of ethanol is added dropwise. The mixture is stirred for 15 hours at room temperature and is then warmed for 2 hours under reflux. The solvent is then distilled off in vacuo and the green residue is dried for 20 hours at 60° C. and 15 mbars. Analysis of the product shows that it contains 6.91% of Ni and 1.27% of water. This corresponds to a molar ratio amine:nickel of 1:1 (m=1) and a molar water content of n=0.59.

EXAMPLE 2

28.7 g of nickel 3,5-di-tert.butyl-4-hydroxybenzoate containing 4.1% of water are dissolved in 250 ml of dry toluene. 12.9 g of n-octylamine are added thereto and the solution is heated to the reflux temperature for 15 hours whilst azeotropically separating off water. After distilling off the solvent in vacuo, the green residue is dried for 20 hours at 60° C. and 15 mbars. The analysis shows that it contains 7.25% of Ni and 0.37% of $H_2O$. This corresponds to a complex with molar proportions $m=2$ and $n=0.17$.

EXAMPLES 3 TO 21

The procedure described in Example 1 is followed, in each case reacting one mol of nickel 3,5-di-tert.butyl-4-hydroxybenzoate (containing 4.1% of $H_2O$) with one mol of the amines mentioned in Table I.

EXAMPLES 22 TO 29

A sodium methylate solution prepared from 2.3 parts of Na and 70 ml of ethanol is added dropwise to a solution consisting of 12.9 parts (0.05 mol) of 3,5-di-tert.butyl-4-hydroxybenzoic acid, 14.2 parts of stearic acid (0.05 mol) and 175 ml of ethanol. After completion of the reaction, stirring is continued for a further ½ hour, and the reaction mixture thus prepared is then slowly added dropwise to a nickel chloride solution consisting of 11.7 parts of $NiCl_2.6H_2O$ (0.05 mol) and 250 ml of ethanol. The mixture is then warmed for 1 hour to the reflux temperature, the NaCl formed is filtered off, the solvent is distilled off in vacuo and the green rsidue is dried for 20 hours at 60° and 15 mm Hg. The analysis of the product shows that it contains 9.8% of Ni and 2.1% of water. This corresponds to the presence of the nickel compound of the formula

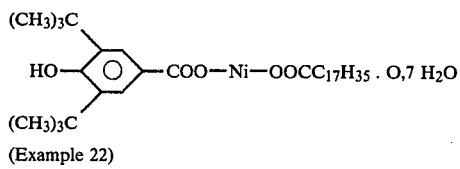

(Example 22)

The compounds of Examples 25–27, listed in Table II, were prepared analogously.

TABLE II $$A = HO - \underset{(CH_3)_3C}{\overset{(CH_3)_3C}{\bigcirc}} - COO^-$$

| Example No. | Formula | Analysis Ni % | H$_2$O % | Molar proportion m | n |
|---|---|---|---|---|---|
| 23 | A—NiOCOC$_{17}$H$_{35}$ . C$_{12}$H$_{25}$NH$_2$ | 7.4 | 1.3 | 1 | 0.55 |
| 24 | A—NiOCOC$_{17}$H$_{35}$ . C$_4$H$_9$NH$_2$ | 8.1 | 1.7 | 1 | 0.62 |
| 25 | A—NiOCOCH$_2$CH$_2$—⟨O⟩(C(CH$_3$)$_3$)—OH (C(CH$_3$)$_3$) | 9.1 | 2.4 | — | 0.8 |
| 26 | A—NiOCO(CH$_2$)$_{10}$—CH(CH$_2$)$_5$CH$_3$ \| OH | 9.6 | 2.4 | — | 0.83 |
| 27 | A—NiOCO(CH$_2$)$_{10}$CH$_3$ | 10.9 | 2.4 | — | 0.70 |
| 28 | A—NiOCO(CH$_2$)$_{10}$CH$_3$ . NH$_2$C$_4$H$_9$ | 9.3 | 2.4 | 1 | 0.79 |
| 29 | A—NiOCO(CH$_2$)$_{10}$CH$_3$ . NH$_2$C$_{12}$H$_{25}$ | 7.9 | 1.7 | 1 | 0.66 |

TABLE I

| Ex. No. | Amine employed | Analysis Ni % | H$_2$O % | Molar proportion m | n |
|---|---|---|---|---|---|
| 3 | n-Butylamine | 9.10 | 3.27 | 1 | 1.18 |
| 4 | n-Octylamine | 8.3 | 1.30 | 1 | 0.5 |
| 5 | tert.Octylamine | 8.37 | 1.65 | 1 | 0.64 |
| 6 | Dodecylamine | 7.54 | 1.18 | 1 | 0.5 |
| 7 | 2-Ethyl-butylamine | 8.64 | 0.91 | 1 | 0.33 |
| 8 | 2-Ethyl-hexylamine | 8.15 | 1.65 | 1 | 0.64 |
| 9 | Benzylamine | 8.48 | 1.15 | 1 | 0.43 |
| 10 | p-Dodecylbenzylamine | 7.11 | 1.50 | 1 | 0.704 |
| 11 | 2,2,6,6-Tetramethylpiperidine | 8.54 | 1.00 | 1 | 0.392 |
| 12 | Morpholine | 9.05 | 0.60 | 1 | 0.216 |
| 13 | Cyclohexylamine | 8.72 | 1.85 | 1 | 0.687 |
| 14 | Aniline | 9.18 | 5.07 | 1 | 1.93 |
| 15 | Dibutylamine | 8.27 | 0.81 | 1 | 0.31 |
| 16 | Dicyclohexylamine | 7.83 | 2.00 | 1 | 0.84 |
| 17 | Dioctylamine | 7.48 | 1.62 | 1 | 0.73 |
| 18 | Didodecylamine | 6.41 | 1.73 | 1 | 0.88 |
| 19 | Dioctadecylamine | 5.48 | 1.28 | 1 | 0.78 |
| 20 | Tributylamine | 8.30 | 2.09 | 1 | 0.88 |
| 21 | Trioctylamine | 6.64 | 1.85 | 1 | 0.95 |

The complexes containing amines, according to Examples 23, 24, 28 and 29, are prepared analogously to Examples 1–21, or by a "one-pot process" in an elaborated process of Example 22: after the reaction mixture has been added to the $NiCl_2.6H_2O$ solution and the whole has been heated for one hour under reflux, the amine L is added, the mixture is then warmed, the NaCl formed is filtered off, the solvent is distilled off in vacuo and the green residue is dried for 20 hours at 60° and 15 mm Hg.

EXAMPLE 30

1,000 parts of polypropylene powder (melt index 1.5 g/10 minutes (230° C., 2,160 g)) are mixed in a drum mixer with 1 part of β-(3,5-di-tert.butyl-4-hydroxyphenyl)propionic acid octadecyl ester and 5 parts of a light stabiliser from the table which follows, and the mixture is subsequently granulated in a Buss Co-kneader at a temperature of 200° C.

The resulting granules are converted to a film in the usual manner, using an extruder with slit dies; the film is out into tapes which are then stretched at an elevated temperature, using a stretching ratio of 1:6, and are wound up (tape gauge: 700–900 den; tensile strength: 5.5–6.5 g/den).

The polypropylene tapes thus prepared are mounted on sample carriers without applying tension and are exposed in a Xenotest 150 apparatus. After various times, groups of 5 specimens are removed and their tensile strength is determined. The measure of the protective action of the individual light stabilisers is the exposure time after which the tensile strength of the tapes has declined to 50% of the original value. The values obtained are listed in Table III.

TABLE III

| Light stabiliser | Hours of exposure to reach 50% tensile strength |
| --- | --- |
| Nickel 3,5-di-tert.butyl-4-hydroxy-benzoate (4.1% of H$_2$O) | 3,850 |
| Compound from Example No. 1 | 3,900 |
| 2 | 3,800 |
| 3 | 4,050 |
| 4 | 3,950 |
| 8 | 4,000 |
| 11 | 4,150 |
| 15 | 4,050 |
| 17 | 4,100 |
| 19 | 3,950 |
| 21 | 3,900 |

EXAMPLE 31

100 parts of polyethylene of density 0.917 are homogeneously mixed with 0.1 or 0.3 part of a light stabiliser of the formula I for 10 minutes at 180° C. in a Brabender plastograph. The mass thus obtained is pressed in a platen press at 170° C. to give 1 mm thick sheets and these are examined visually for undissolved constituents. The sheets are suspended at room temperature and periodically examined for signs of efflorescence. The results are summarised in Table IV.

TABLE IV

| Light stabiliser | Solubility | | Compatibility$^x$ | |
| --- | --- | --- | --- | --- |
|  | 0.1% of LM | 0.3% of LM | 0.1% of LM | 0.3% of LM |
| Nickel 3,5-di-tert.butyl-4-hydroxy-benzoate (4.1% of H$_2$O) | Not dissolved | — | — | |
| Compound from |  |  |  |  |
| Example 1 | Dissolved | Dissolved | >105 | >105 |
| Example 6 | Dissolved | Dissolved | >420 | >420 |
| Example 8 | Dissolved | Dissolved | >280 | >280 |
| Example 9 | Dissolved | Dissolved | >280 | >280 |
| Example 12 | Dissolved | Dissolved | >280 | >280 |
| Example 13 | Dissolved | Dissolved | >280 | >280 |
| Example 17 | Dissolved | Dissolved | >280 | >280 |
| Example 20 | Dissolved | Dissolved | >280 | >280 |
| Example 24 | Dissolved | Dissolved | >280 | >280 |
| Example 26 | Dissolved | Dissolved | >280 | >280 |

TABLE IV-continued

| Light stabiliser | Solubility | | Compatibility$^x$ | |
| --- | --- | --- | --- | --- |
|  | 0.1% of LM | 0.3% of LM | 0.1% of LM | 0.3% of LM |
| Example 27 | Dissolved | Dissolved | >280 | >280 |

$^x$Compatibility: Number of days after which no signs of efflorescence are detectable.

What we claim is:

1. A compound of the formula I

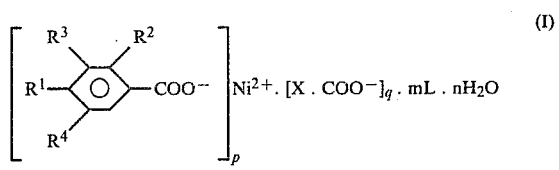

wherein either $R^1$ is hydroxyl and $R^2$ is hydrogen or $R^1$ is hydrogen and $R^2$ is hydroxyl, $R^3$ and $R^4$ are hydrogen or alkyl with 1–5 C atoms, either p is 1 and q is 1 or p is 2 and q is zero, X is optionally hydroxyl-substituted alkyl, cycloalkyl, aryl, alkaryl or aralkyl, m is a value from 1–2 and, n represents a value from 0 to 2 and L denotes a ligand $R^5$—N($R^6$)—$R^7$, in which $R^5$ and $R^6$ together with the N atom form a morpholine ring which is substituted by alkyl groups or is unsubstituted and $R^7$ is H, alkyl or aralkyl.

2. The compound according to claim 1, of the formula I, wherein $R^1$, $R^2$, $R^3$, $R^4$, m and n have the above mentioned meaning and L denotes a ligand $R^5$—N($R^6$)—$R^7$, in which $R^5$ and $R^6$ together with the N atom form a morpholine ring, which is substituted by methyl groups or is unsubstituted, and $R^7$ is H, alkyl with 1–8 C atoms or aralkyl with 7–11 C atoms and either p is 1 and q is 1 or p is 2 and q is zero, and X is alkyl or hydroxyalkyl with 1–22 C atoms, cycloalkyl with 4–10 C atoms, phenyl which is optionally substituted by alkyl with 1–4 C atoms or hydroxyl, or phenylalkyl with 7–16 C atoms.

3. The compound of the formula I according to claim 1, wherein either $R^1$ represents a hydroxyl group and $R^2$ represents hydrogen or $R^1$ represents hydrogen and $R^2$ represents a hydroxyl group, $R^3$ and $R^4$ represent hydrogen or alkyl with 1 to 5 C atoms, m represents a value from 1 to 2 and n represents a value from 0 to 2 and L denotes a ligand of the formula $R^5$—N($R^6$)—$R^7$, in which $R^5$ and $R^6$ together with the N atom form a morpholine ring which is substituted by alkyl groups or is unsubstituted, and $R^7$ is H, alkyl or aralkyl, and p is 2 and q is zero.

4. The compound according to claim 3, wherein $R^5$ and $R^6$ together with the N atom form a morpholine ring which is substituted by methyl groups or is unsubstituted, and $R^7$ is H, alkyl with 1 to 8 C atoms or aralkyl with 7 to 11 C atoms.

5. The compound of claim 1 of the formula

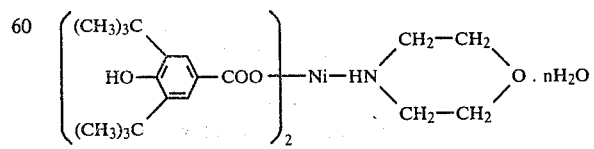

* * * * *